United States Patent [19]
Johnson

[11] Patent Number: 5,715,831
[45] Date of Patent: Feb. 10, 1998

[54] CALIBRATED AIR TUBE FOR SPIROMETER

[75] Inventor: Michael O. Johnson, Derry, N.H.

[73] Assignee: Desert Moon Development Limited Partnership, Dana Point, Calif.

[21] Appl. No.: 670,192

[22] Filed: Jun. 21, 1996

[51] Int. Cl.⁶ .................................................. H61B 5/08
[52] U.S. Cl. ........................ 128/725; 128/720; 128/726
[58] Field of Search .................................. 128/716, 720, 128/724, 725, 730, 721, 719

[56] References Cited

U.S. PATENT DOCUMENTS

| | | |
|---|---|---|
| D. 272,184 | 1/1984 | Karpowicz . |
| 4,122,842 | 10/1978 | Pikul . |
| 4,282,425 | 8/1981 | Chadima, Jr. et al. . |
| 4,403,514 | 9/1983 | Osborn . |
| 4,570,057 | 2/1986 | Chadima, Jr. et al. . |
| 4,640,293 | 2/1987 | Garbe . |
| 4,807,641 | 2/1989 | Boehringer et al. . |
| 4,856,530 | 8/1989 | Vandervelden ............... 128/692 |
| 4,894,523 | 1/1990 | Chadima, Jr. et al. . |
| 4,905,709 | 3/1990 | Bieganski et al. . |
| 4,989,456 | 2/1991 | Stupecky . |
| 4,995,400 | 2/1991 | Boehringer et al. . |
| 5,021,642 | 6/1991 | Chadima, Jr. et al. . |
| 5,038,621 | 8/1991 | Stupecky . |
| 5,038,773 | 8/1991 | Norlien et al. . |
| 5,060,655 | 10/1991 | Rudolph . |
| 5,081,343 | 1/1992 | Chadima, Jr. et al. . |
| 5,095,197 | 3/1992 | Chadima, Jr. et al. . |
| 5,111,827 | 5/1992 | Rontala . |
| 5,137,026 | 8/1992 | Waterson et al. . |
| 5,144,119 | 9/1992 | Chadima, Jr. et al. . |
| 5,144,121 | 9/1992 | Chadima, Jr. et al. . |
| 5,182,441 | 1/1993 | Chadima, Jr. et al. . |
| 5,187,355 | 2/1993 | Chadima, Jr. et al. . |
| 5,187,356 | 2/1993 | Chadima, Jr. et al. . |
| 5,196,684 | 3/1993 | Lum et al. . |
| 5,218,191 | 6/1993 | Chadima, Jr. et al. . |
| 5,233,175 | 8/1993 | Chadima, Jr. et al. . |
| 5,258,606 | 11/1993 | Chadima, Jr. et al. . |
| 5,277,195 | 1/1994 | Williams . |
| 5,277,196 | 1/1994 | Hankinson et al. . |
| 5,287,851 | 2/1994 | Beran et al. . |
| 5,288,318 | 2/1994 | Mayer et al. . |
| 5,288,985 | 2/1994 | Chadima, Jr. et al. . |
| 5,292,782 | 3/1994 | Bastioli et al. . |
| 5,296,526 | 3/1994 | Delrue et al. . |
| 5,305,762 | 4/1994 | Acorn et al. . |
| 5,308,966 | 5/1994 | Danielson et al. . |
| 5,319,181 | 6/1994 | Shellhammer et al. . |
| 5,379,650 | 1/1995 | Koford et al. . |

OTHER PUBLICATIONS

Advance for Respiratory Managers (Aug. 1996).
DuPont Material Safety Data Sheet Nomex®, Aramid Fiber (Nov. 1993).
Respiradyne®, Pulmonary Function/Ventilation Monitor Operation Manual (1990).
MultiSPIRO–SX Specifications (Date unknown).

*Primary Examiner*—Jennifer Bahr
*Assistant Examiner*—Stephen Huang
*Attorney, Agent, or Firm*—Kenton R. Mullins; Frank J. Uxa

[57] ABSTRACT

The present air tubes include a resistive element which is located in the hollow space of the tubular portion. This resistive element is adapted for providing a linear resistance-versus-pressure response is sized and adapted to cause a pressure difference or differential as air flows in the hollow space across this element. The resistive element includes a planar member having a first face and a second face, and a circular parameter connecting the first face to the second face. An aperture is formed in a center of the planar member for connecting the first face to the second face. A plurality of slots in the planar member extend radially from the aperture, thereby forming a plurality of hinged windows in the planar member. Each of the slots includes a central end and a distal end. The resistive element further includes a plurality of hinge slots. Each hinge slot is connected to a distal end of a slot, and extends generally perpendicularly to an axis of the slot. A total number of hinge slots corresponds to a total number slots.

13 Claims, 7 Drawing Sheets

CALIBRATED AIR TUBE FOR SPIROMETER

BACKGROUND OF THE INVENTION

The present invention relates to air tubes for use with spirometers, and to spirometers using such air tubes. More particularly, the present invention relates to air tubes which are disposable and at least partially biodegradable, and to calibration techniques for ensuring a high level of accuracy when the disposable air tubes are used with the spirometers.

Spirometers are devices used to measure the volume and flow rate of gas exhaled and inhaled by a user or patient, for example, a human being. Two general types of spirometers measure volume and flow, respectively. For the flow type, the actual port of the spirometer used to measure flow is the pneumotach of which Fleisch is one type. These measurements are important for physiological studies and for diagnostic analysis of the pulmonary performance of the spirometer user. For example, the effects of various medicines used to treat patients with pulmonary or asthmatic problems can be analyzed by monitoring the volume and flow rate of gas exhaled before and after the administration of medication. Several devices are available on the market which are known as pneumotachs, such as the Fleisch Pneumotach. These devices depend on a laminar air flow past a resistance element. Other spirometers employ more sophisticated electronics so that laminar flow is not needed.

Measuring the pressure difference or differential pressure of exhaled gas across an element which creates or causes the pressure difference is the basis for differential pressure spirometers. In such differential pressure spirometers, it is important that the air tube (pneumotach) be precisely configured and positioned, for example, relative to the pressure sensing and electronics systems of the spirometers so that measurements can be reliably and reproducibly made. Such precisely configured pneumotachs, rather than being disposable, are made out of metals or durable plastics to be long lasting and effective after many uses without structural degradation. See, for example, Waterson et al U.S. Pat. No. 5,137,026, the disclosure of which is hereby incorporated in its entirety by reference herein.

Since most spirometers involve passing exhaled gas directly from the respiratory system of a user into the instrument for measuring, one important complication of using such devices is contamination from one patient to another patient if the same spirometer is employed by both. Various approaches to overcoming this contamination problem have been suggested. A particularly popular approach is to use a disposable mouthpiece and/or bacterial filter over the inlet to the spirometer. The patient using the spirometer comes in contact only with the mouthpiece and/or bacterial filter and is able, at least in theory, to avoid contaminating the remainder of the device. Drawbacks to this approach include the relative expense of such mouthpieces/filters, and the relative inefficiency of such systems.

Another approach to overcoming this contamination problem is to sterilize in-between patients the portion or portions of the spirometer which come in contact with the user and/or exhaled air. Drawbacks to this approach include having to spend additional capital on sterilization equipment and supplies, having to monitor the operation and efficacy of the sterilization equipment, and having to purchase relatively durable and expensive spirometers to withstand the sterilization procedures.

A third alternative that has been suggested is the use of disposable spirometer components. See, for example, Norlien et al U.S. Pat. No. 5,038,773; Acorn et al U.S. Pat. No. 5,305,762; Karpowicz U.S. Pat. No. Des. 272,184; Boehringer et al U.S. Pat. No. 4,807,641; and Bieganski et al U.S. Pat. No. 4,905,709. Such previous disposable spirometer components have generally been made out of durable plastics or medical grade metals so that, even though they are disposable, the cost of producing such components is relatively high. In addition, such disposable components are relatively difficult to dispose of, for example, because they are made of durable and long lasting materials.

The economical manufacture of a relatively inexpensive spirometer component from a low cost and/or biodegradable material, however, has heretofore been prohibitive because of, for example, quality control concerns. General industry specifications require high quality spirometer components but the quality of these components can decrease as the components are made biodegradable, for example, placement of these components within the spirometer can also present problems. The placement of the resistive element within each air tube can affect the performance of the overall spirometer, for example. The resistive element should be placed in a normal or perpendicular configuration relative to the interior wall of the air tube and, further, should be placed at exact, predetermined distances from the two opposing ends of the air tube. Prior art resistive elements often do not exhibit linear resistance-versus-flow-rate responses. More particularly, resistive elements configured to exhibit good resistance at high flow rates often do not perform adequately at low flow rates and, on the other hand, resistive elements configured to perform well at low flow rates often do not provide ideal resistance at high flow rates. Thus, any possibility of manufacturing a relatively inexpensive spirometer, as an alternative to the existing durable plastic or metal non-biodegradable components of the prior art, would appear to be vitiated due to manufacturing and performance concerns. These manufacturing concerns include the inconsistencies between various disposable, biodegradable spirometer components that may be produced on an assembly line and, further, include subsequent performance variances between the spirometer components resulting from these inconsistencies.

Inconsistencies in these components may be augmented when they are assembled together or placed into the spirometer. For example, a throughport of an air tube may not be perfectly formed, and the subsequent placement of this throughport onto the spirometer may introduce abnormally low pressure readings due to air leakage around the pressure port. Even placement of the resistive element within the air tube, as another example, may not be exact between various assemblies and, accordingly, a problem of accuracy may even be prevalent among existing durable plastic or metal non-biodegradable components as well. Accordingly, it would be advantageous to provide a means of ensuring high performance quality and consistency between various spirometer components from an assembly line, regardless of whether the spirometer components are metal, plastic, or biodegradable,

SUMMARY OF THE INVENTION

New calibrated air tubes for use in spirometers and spirometers including such calibrated air tubes have been discovered. The present calibrated air tubes are disposable so that after use by a patient, they are removed from the spirometer and disposed. The air tubes are almost completely biodegradable, can be manufactured relatively economically, and are capable of yielding high and consistent performance characteristics.

As used herein, the term "biodegradable" means that the component or material is decomposable into more environmentally acceptable components, such as carbon dioxide, water, methane and the like, by natural biological processes, such as microbial action, for example, if exposed to typical landfill conditions, in no more than five years, preferably no more than three years, and still more preferably no more than one year.

Having the calibrated air tube biodegradable provides substantial advantages. First, when the air tube and resistive elements are disposed of, the burden on the environment of such disposal is reduced relative to, for example, a non-biodegradable air tube, such as those made out of conventional plastics or metals. In addition, because the air tube and resistive elements are biodegradable, they can be made of materials which are inexpensive and plentiful (readily available). Thus, the present air tubes are relatively inexpensive, easy and straightforward to produce. Subsequent calibration of the air tubes accounts for any discrepancies in size, shape, and performance of the air tubes.

Since the present air tubes can be made economically, replacing a used air tube with a new air tube is done without substantial economic impact. In addition, the present air tubes can be replaced in the spirometer very easily. These advantages promote operator compliance in that the spirometer operator (for example, the care provider or the patient operating the spirometer) is more likely to change the present air tubes after each patient or treatment, thus reducing the risks of contamination and the spread of diseases, for example, tuberculosis and other respiratory system disorders, AIDS, other systemic conditions and the like.

Spirometers employing the present calibrated air tubes provide cost effective, reliable and reproducible (from air tube to air tube) measurements of the pulmonary performance of the user, with reduced risk of contamination. In short, the present disposable, biodegradable calibrated air tubes are inexpensive and easy to produce to acceptably precise specifications (for reproducible performance), are effective and reliable in use, and are conveniently and effectively disposed of in an environmentally acceptable or safe manner to reduce the risks of contamination caused by spirometer use.

DETAILED DESCRIPTION OF THE DRAWINGS

Figures 1, 1A:
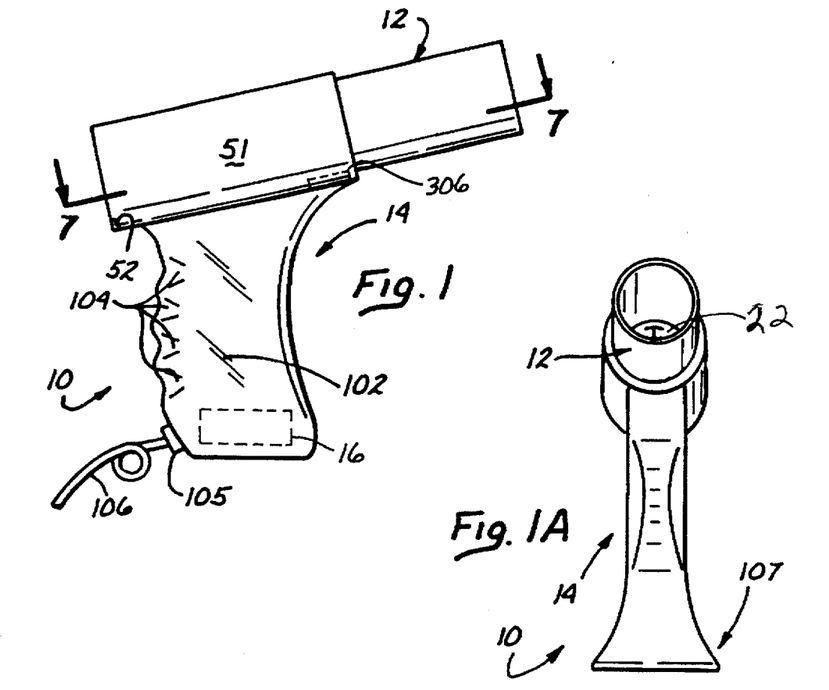
FIG. 1 is a side view of a spirometer in accordance with the present invention showing a portion of the electronics disposed apart from the hand held unit.
FIG. 1A is a front side view of the spirometer shown in FIG. 1.

Referring to FIGS. 1 and 1A, a spirometer in accordance with the present invention, shown generally at 10, includes a disposable, biodegradable air tube 12, a housing 14 and control electronics 16. Spirometer 10 is what is commonly known as a differential pressure spirometer and, in general, operates in a manner similar to the spirometer disclosed in the above-noted Waterson et al U.S. Pat. No. 5,137,026.

Figure 2:
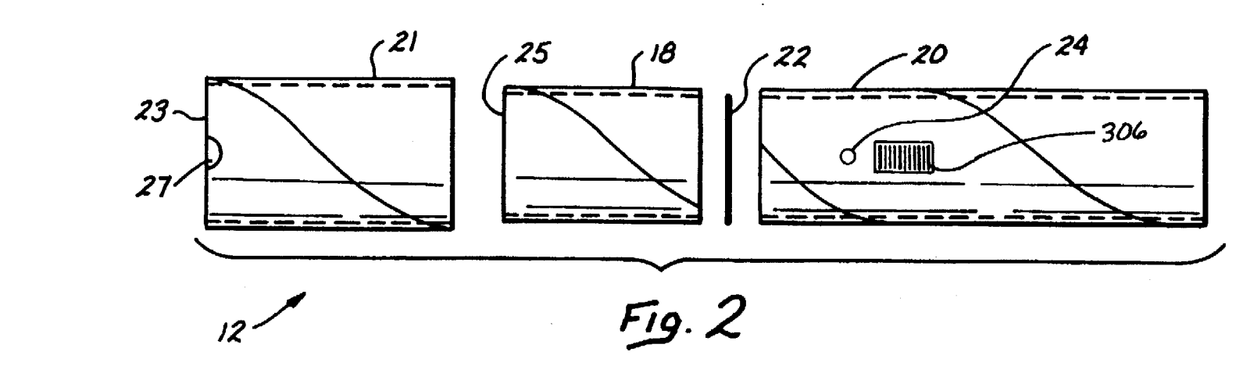
FIG. 2 is an exploded view of the air tube of the present invention.

The air tube 12 is described with reference to FIGS. 2 and 3. The air tube 12 includes a first tubular segment 18, a second tubular segment 20, and a collar tube 21. A resistive element 22 fits between the first tubular segment 18 and the second tubular segment 20. The air tube 12 and resistive element 22 are preferably approximately ninety-nine percent biodegradable. The tubular segments 18, 20, and 21 are made of biodegradable cardboard or heavy paper, for example, in a manner similar to how cardboard tubes are conventionally made, such as for use with bathroom tissue and the like products. These segments 18, 20, and 21 are preferably coated with a glossy layer. The resistive element 22 preferably comprises biodegradable material having good memory characteristics. As presently embodied, the resistive element 22 comprises a Nomex material. The resistive element 22 material may, alternatively, comprise any nylon or other material which is somewhat resistant to moisture. As presently embodied, the resistive element 22 is approximately 0.003 inches thick, but other thicknesses may be used according to design parameters.

The resistive element 22 is first secured to either the first tubular segment 18 or the second tubular segment 20, and then the other tubular segment 18 or 20 is then secured to the resistive element 22. A biodegradable adhesive is preferably used. As presently embodied, an outer diameter of the first tubular segment 18 is equal to an outer diameter of the second tubular segment 20, and the outer diameter of the resistive element 22 is equal to the outer diameter of the first tubular segment 18.

An inner diameter of the collar tube 21 is approximately equal to the outer diameter of the first tubular segment 18. The collar tube 21 is adapted to fit over both the first tubular segment 18 and the second tubular segment 20. Although adhesives are preferably used for securing the resistive element 22 between the first tubular segment 18 and the second tubular segment 20, the close, frictional fit of the collar tube 21 over the first tubular segment 18 and the second tubular segment 20 may be sufficient, alone, to secure the resistive element 22 between the first tubular segment 18 and the second tubular segment 20.

The distal end 23 of the collar tube 21 is flush with the distal end 25 of the first tubular segment 18, when the collar tube 21 is properly secured over both the first tubular segment 18 and the second tubular segment 20. Additionally, a notch 27, which preferably comprises a punched out semicircle in the distal end 23 of the collar tube 21, is preferably lined up with a port 24 of the second tubular segment. The port 24 of the second tubular segment 20 preferably comprises a punched out circle in the second tubular segment 20. The notch 27 and/or the port 24 may be formed in the collar tube 21 and/or the second tubular segment 20 either before or after assembly of the three pieces 18, 20, and 21. After assembly of the three elements 18, 20, and 21. The port 24 opens directly into a hollow space (FIG. 3) of the air tube 12.

Figure 3:
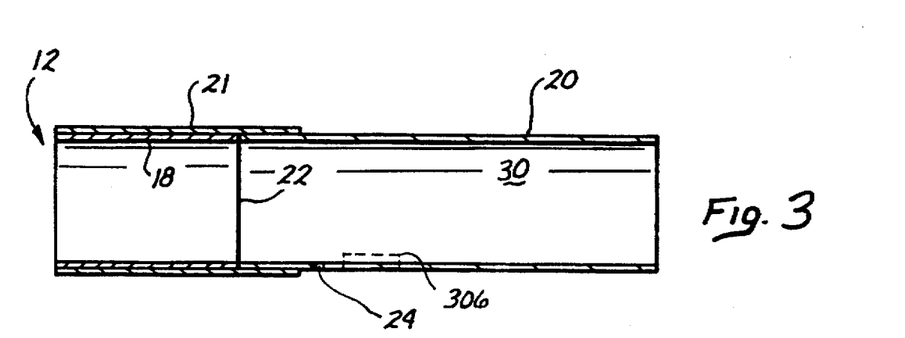
FIG. 3 is a cross-sectional view of the air tube of the present invention.

FIG. 3 illustrates the air tube 12 in an assembled state. Although a three piece configuration of the air tube 12 is presently preferred, these three pieces 18, 20, and 21 may be replaced by a single tube, for example, and/or the resistive element 22 may be secured to an annular ring (not shown), which is inserted within the single tube.

Figures 4, 5:
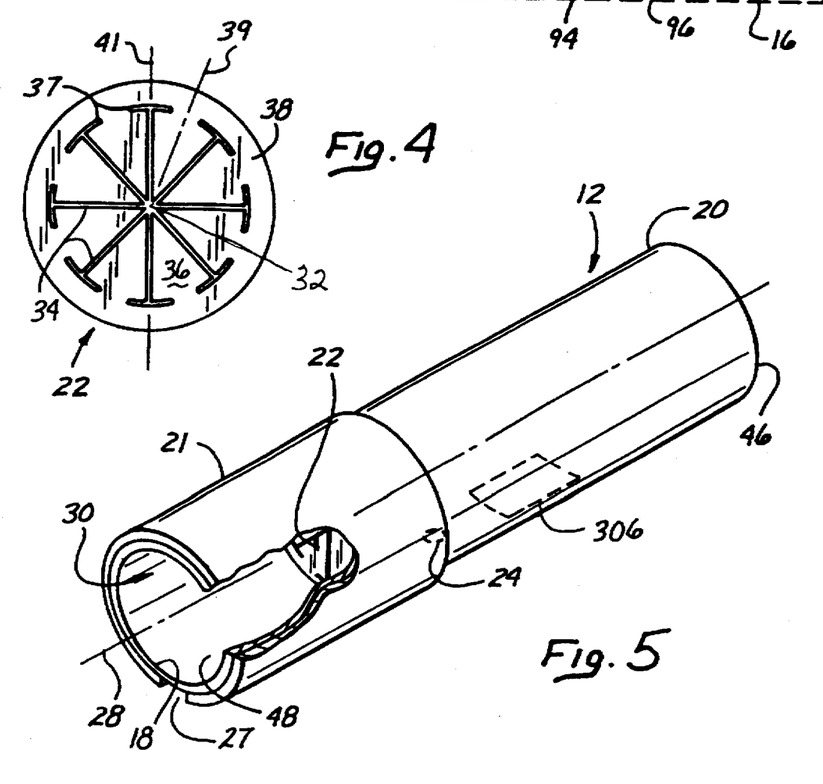
FIG. 4 is a top planar view of the resistive element of the present invention.
FIG. 5 is a partially cut away, top front view, in perspective, of the air tube used in the spirometer shown in FIG. 1.

FIG. 4 illustrates a top planar view of the resistive element 22, according to the presently preferred embodiment. The resistive element 22 comprises a center aperture 32 and a plurality of slots 34 extending radially from the center aperture 32. Each pair of adjacent slots 34 forms a hinged window 36, which as presently embodied comprises an arrowhead shape. Each arrowhead-shaped hinged window 36 comprises a point located near the center aperture 32 and a neck 38 located distally of the center aperture 32. As presently embodied, the resistive element 22 comprises eight hinged windows 36, but greater or fewer numbers of hinged windows 36 may be used according to design parameters. The width of each neck 38 controls the flexibility of the corresponding hinged window 36. A larger neck renders the corresponding hinged window 36 less flexible, and a smaller neck 58 renders the corresponding hinged window 36 more flexible.

A human patient blowing into an end of the air tube 12 generates an air flow through the resistive element 22 which, typically, may comprises an air flow rate of between zero and 16 liters per second. The resistance provided by the resistive element 22 should, ideally, be approximately linear among these various air flow rates. Prior art resistive elements, comprising a disk with a single aperture therein, for example, do not have linear pressure versus flow rate relationships. A prior art disk shaped resistive element having a good resistance of less than 1.5 centimeters of water per liter per second at approximately 12 liters per second, for example, will not have a good resistance at lower flow rates. More particularly, such a conventional disk shaped resistive element would have a very low resistance at low flow rates, which is unacceptable.

The resistive element 22 of the present invention utilizes unique hinged windows 36 having necks 38, which can be engineered to tailor the resistance of the resistive element 22 at various flow rates. The resistive element 22 of the present invention is adapted to provide an ideal resistance of less than 1.5 centimeters of water per liter per second at a flow rate of approximately 12 liters per second but, in contrast to a conventional disk shaped resistive element, the resistive element 22 of the present invention also provides good resistance at low flow rates. Generally speaking, the resistive element 22 provides a very good, approximately linear flow-rate-versus-resistance response for flow rates between zero and 16 liters per second. At high flow rates, the hinged windows 36 open widely to provide a good resistance that is not too high. At low flow rates, the hinged windows 36 open very little, to thereby provide a good resistance that is not too low.

According to the presently preferred embodiment, an angle between two of the slots 34 is approximately 45 degrees, and each of the slots 34 has a width of approximately 0.02 inches. A preferred width of each of the perpendicular hinged portions 37, which is used to control the width of a neck 38, is approximately 0.04 inches. The diameter of the resistive element 22 is preferably 1.09 inches plus or minus 0.0005 inches, and a width between a line 39 bisecting one of the hinged windows 36, and another line 41 passing through a slot 34 is approximately 0.0625 inches plus or minus 0.005 inches.

One important element of the resistive element 22 of the present invention is the resistance supplied at low flow rates, since, typically, unhealthy patients are unable to generate high flow rates. The same resistive element also functions well at high flow rates. The resistive element 22 provides good resistance at various flow rates, regardless of whether the patient is exhaling or inhaling.

Referring to FIG. 5, air tube 12 includes an open inlet 46 and an open outlet 48. The area surrounding the open inlet 46 is sized and adapted to be fitted into a human being's mouth. This mouthpiece area is employed by the patient using spirometer 10 (FIG. 1) by placing the area 46 into the mouth and exhaling into hollow space 30 of the air tube 12.

Figure 6:
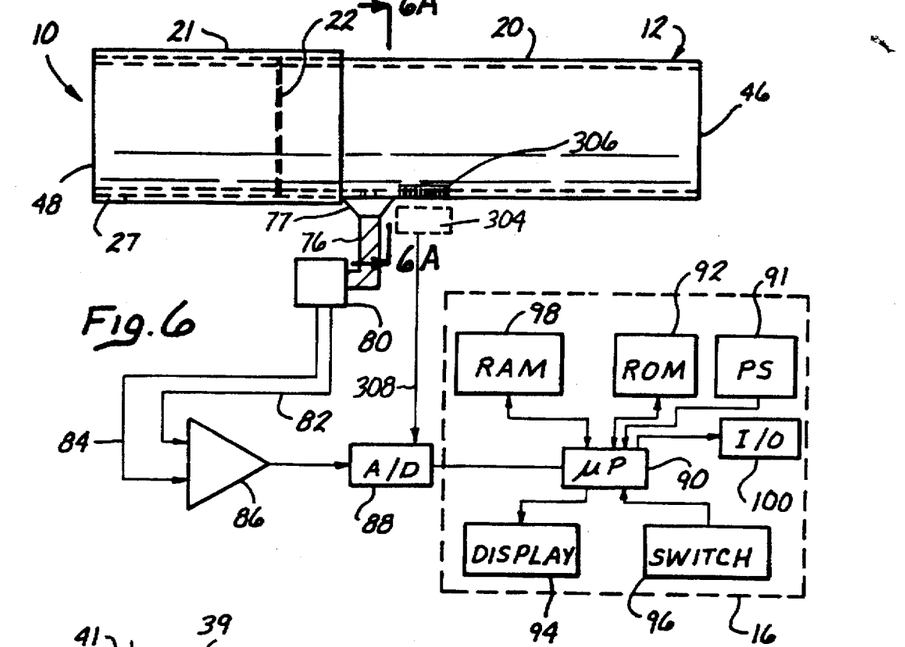
FIG. 6 is a somewhat schematic illustration showing a spirometer in accordance with the present invention.

Turning back to FIG. 1, when it is desired to use air tube 12, it is unpackaged and is coupled to housing 14. In particular, the air tube 12 is coupled to the housing tube 51. The housing tube 51 includes a tab 52, which is adapted to fit within the notch 27 (FIG. 2) of the air tube 12. Before the air tube 12 is placed into the housing tube 51, the notch 27 is aligned with the port 24 (FIG. 2) and, as presently embodied, is manually aligned by the user just before insertion into the housing tube 51. When the notch 27 is aligned with the port 24, the port 24 will align with the pressure sensing leg 76, as shown in FIG. 6. More particularly, a fitting of the pressure sensing leg 76, which preferably comprises a suction cup shape 77 which fits around the port 24 for an airtight fit. The suction cup shaped fitting 77 preferably comprises silicone rubber or vinyl, and is adapted to provide a good fit around the port 24, to thereby attenuate any leakage of air at this interface. Consequently, breath from the patient is not introduced into the pressure sensing leg 76 and contamination of the pressure sensing leg 76 is avoided.

After the notch 27 of the air tube 12 is placed within the housing tube 51 and, more particularly, placed over the alignment tab 52, the distal end 23 of the collar tube 21 should be flush with the distal end of the housing tube 51. At this point, spirometer 10 is ready for use. Note that air tube 12 is longer than housing tube 51 and, when properly coupled to the housing tube, extends beyond one end of the housing tube. The relatively long air tube 12 reduces the risk of air exhaled from the spirometer user coming into effective contact with and contaminating the housing.

FIG. 6 illustrates the general operation of a spirometer, shown generally at 10. The following is a general description of the operation of the spirometer 10 after the air tube 12 is properly located and positioned relative to the pressure sensing leg 76. The calibration method and apparatus of the present invention will subsequently be discussed in further detail after the general operational overview now provided. This general description is applicable using any spirometer, such as spirometer 10, in accordance with the present invention. Through port 24 (FIG. 2) communicates with pressure sensing leg 76. As a further protection against contamination, pressure sensing leg 76 may be equipped with a filter, although this is not required. The pressure sensing leg 76 communicates with a differential or "gauge" type pressure transducer 80, which may be, for example, a transducer sold by Motorola under the trademark MPX 2020D. The pressure transducer 80 generates an electrical signal on a pair of output wires 82 and 84, which signal is proportional to the differential pressure between pressure sensing leg 76 and a sensed atmosphere pressure. This signal is amplified by a differential amplifier stage 86 and fed into an analog-to-digital convertor 88 which converts the amplifier output into digital signals.

The output from convertor 88 is fed to a microprocessor 90, which is part of control electronics 16. The microprocessor 90 uses calibration data supplied by coded information on the air tube 12 in combination with an algorithm stored in a ROM 92 to perform several calculations on the signal from convertor 88, and to display the calibrated final results, e.g., volume and flow rate, on display 94, for example, a conventional monitor or liquid crystal display module. Microprocessor 90 is powered by a power source 91, for example, either a battery or a connector capable of being coupled or connected to a source of conventional electric line voltage. Switch 96 can be activated to initiate the operation of the spirometer through microprocessor 90. The results during each measurement may be stored in a RAM 98 for future reference. An input/output port 100 may also be provided to allow for changing the programming of the microprocessor 90. Furthermore, the microprocessor 90 may be programmed so that on command it may download the results accumulated in RAM 98 through input/output port 100 to a printer or a computer. Waterson et al U.S. Pat. No. 5,137,026 provides details regarding the operation of a conventional spirometer. When a patient has concluded one treatment or diagnostic exercise using the spirometer 10, the biodegradable air tube 12 is removed from the housing tube and is disposed of in an environmentally safe manner.

As shown in FIGS. 1 and 1A, the housing 14 is structured to be gripped in one hand of the user. For example, the shaft 102 of housing 14 is configured for easy hand gripping. In addition, finger indents 104 are provided to make hand holding this device even easier.

The embodiment shown in FIGS. 1 and 1A includes control electronics 16 located within the hand held housing 14. Communication with external computers or printers can occur through cable 106 which can be connected to the convertor using a jack 105, such as a conventional RJ-11 quick connect jack, on housing 14. As presently preferred, communication can also occur through an additional infrared data association (IRDA) link, which is conventional, and operable between the housing 14 and the external computer or printer. The electronics in the housing 14 are preferably powered by a battery pack, such as a conventional rechargeable nickel-cadmium battery. If such a battery pack is used, the housing 14 includes a port through which the battery pack can be charged.

In the embodiment shown in FIGS. 1 and 1A, microprocessor 90 can be a dedicated microprocessor including a transparent-overlay keypad structured and adapted specifically to control the operation of a spirometer. Alternatively, the microprocessor 90 may be a component of a general purpose, personal computer including a full-sized keyboard, video monitor, hard disk drive and printer. The dedicated microprocessor is particularly advantageous because of its relative simplicity, reduced cost and ease of use. In addition, the shaft 102 of housing 14 includes a tapered portion 107, as shown in FIG. 1A, which facilitates placing and maintaining the housing on a flat surface, for example, between uses.

Figure 7:
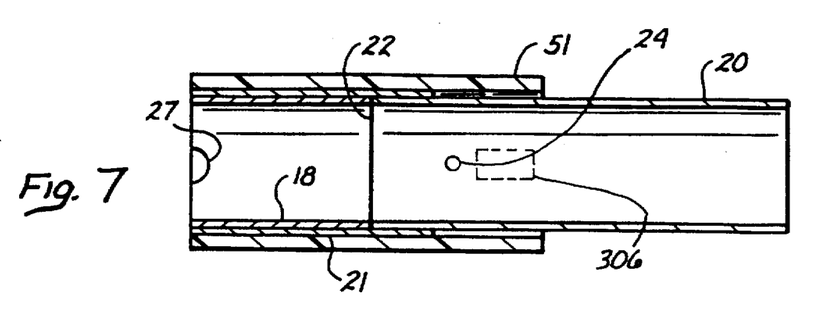
FIG. 7 is a cross-sectional view taken generally along line 7—7 of FIG. 1.

The embodiment shown in FIGS. 1 and 1A is useful as a completely new spirometer, or the air tube 12 and housing 14 can be used to retrofit an existing spirometer. For example, an existing spirometer includes a hand held unit including a permanent breathing tube, pressure sensing leg, a pressure transducer, an amplifier and an analog-to-digital convertor, and is connected to a dedicated control system, which functions in a manner substantially similar to control electronics 16. Simply by replacing the existing hand held unit with housing 14 and the components coupled to or disposed in the housing, a retrofitted spirometer is produced which has many of the advantages of the present invention. FIG. 7 shows a cross-sectional view of the spirometer 10 of FIG. 1, taken along line 7—7 of FIG. 1.

Figure 8:
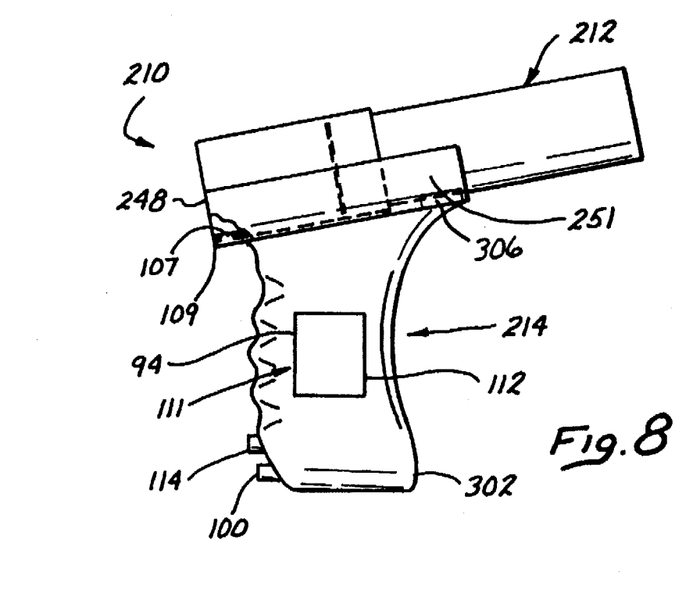
FIG. 8 is a side view of an alternative embodiment of a spirometer in accordance with the present invention.
Figure 9:
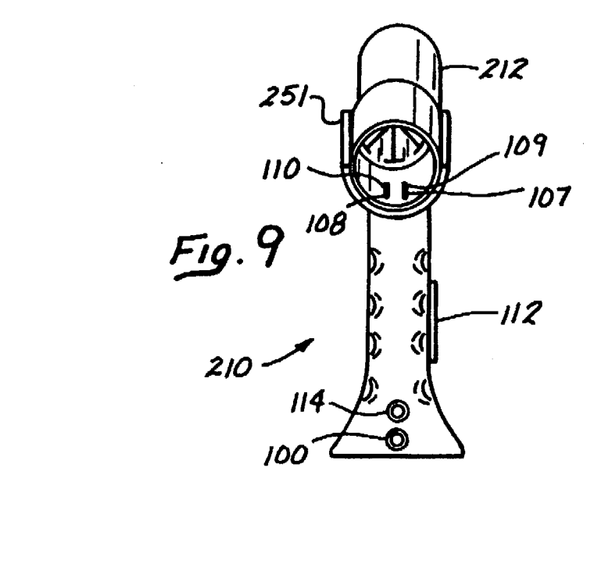
FIG. 9 is a back side view of the spirometer shown in FIG. 8.

Another embodiment is illustrated in FIGS. 8 and 9. This spirometer, shown generally at 210, is, except as expressly stated herein, structured in a manner similar to spirometer 10. Components of spirometer 210 which correspond to components of spirometer 10 have corresponding reference numerals increased by 200.

The primary differences between spirometer 210 and spirometer 10 have to do with the configuration of air tube 212 and the configuration of the housing tube 251. Air tube 212 is structured substantially similar to air tube 12 except that in the region near open outlet 248, two positioning ports 107 and 108 are provided. Housing tube 251 is structured to act as a cradle for air tube 212 rather than surrounding the air tube 212, as does housing tube 51. In addition, housing tube 251 includes two upwardly extending projections 109 and 110 which are positioned to be received by positioning ports 107 and 108, respectively, when air tube 212 is coupled to housing tube 251. With projections 109 and 110 mated to or received by positioning ports 107 and 108, the port 224 (not shown) is properly aligned with the pressure sensing leg 276 (not shown).

As shown in FIGS. 8 and 9, a transparent-overlay control keypad 112 of microprocessor 90 is located on the shaft 302 of housing 214. In addition, this embodiment preferably comprises greater ROM, and the display 94 is located on the housing 214 beneath the transparent-overlay keypad 112. In spirometer 210, the power source 91 is a battery pack, such as a conventional rechargeable nickel-cadmium battery, and is located within housing 214. Port 114 on housing 214 is adapted to provide communication between battery pack 91 and a conventional battery charger to recharge the battery pack when needed. I/O port 100 is also carried by housing 214 and provides convenient communication between microprocessor 90 and a computer or printer, when it is desired to download information from electronic circuitry 111 to such other device. As with the embodiment of FIG. 1, an IRDA optical port is also disposed on the shaft 302. Spirometer 210 is a self-contained unit that can be operated by a single patient.

In order to operate spirometer 210, air tube 212 is coupled to housing tube 251 so that projections 109 and 110 mate with positioning ports 107 and 108, respectively. The patient then activates a switch on the transparent-overlay keypad 112 and uses spirometer 210 for any treatment and/or diagnostic procedure desired. When it is desired to remove air tube 212 from housing tube 251, the biodegradable air tube 212 is simply picked up from the housing tube 212 and can be discarded in an environmentally acceptable manner. Referring again to FIG. 6, a character recognition unit 304 is disposed within the housing 14 of the spirometer 10. The character recognition unit 304 preferably comprises a device for recognizing bar-code-like stripes. The character recognition unit 304 is disposed within the housing 14 to align with a character sequence 306, preferably bar-code-like stripes, on the air tube 12, when the air tube 12 is placed within the housing 14. According to the present invention, calibration information relating to the air tube 12 is coded within the character sequence 306. This coded information is read by the character recognition unit 304 and is conveyed to the converter 88 via line 308 and then to the microprocessor 90. The converter 88 preferably comprises eight inputs. Of these eight, two receive pressure transducer 80 signals, one receives flow tube pressure, and one if for rhinomanometry (nasal air pressure). As presently embodied, the character recognition unit 304 is disposed within the housing 14 of the spirometer 10 to automatically read the character sequence 306, but, alternatively, this reading of information from the character sequence 306 may be performed manually. Human-readable characters may be disposed next to the character sequence 306, for example. Additionally, the reading of information from the character sequence 306 may be performed before, during, or after each reading by the spirometer 10, according to design preference.

The character recognition unit 304 is preferably an optical character recognition unit, adapted for reading a bar code character sequence 306 but, alternatively, other information conveying techniques may be implemented. For example, magnetic character recognition, optical alphanumeric character recognition, optical symbol recognition, etc. may be used, so long as calibration information relating to the air tube 12 is conveyed to the microprocessor 90. Preferably, the character recognition unit 304 comprises a linear array for recognizing bar-type codes.

Figures 6A, 12:
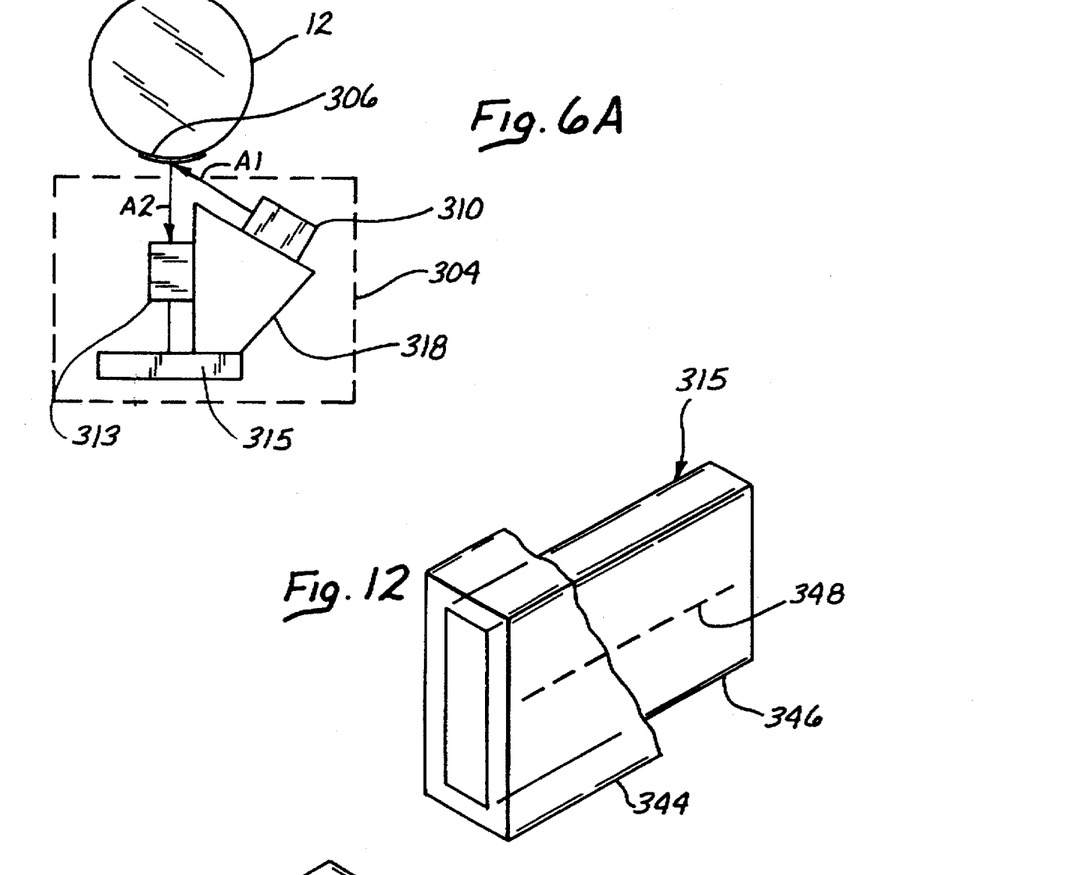
FIG. 6A is a cross-sectional view taken generally along line 6A—6A of FIG. 6.
FIG. 12 is a schematic representation of a linear array of photodiodes for receiving light from a bar code label according to the presently preferred embodiment.

FIG. 6A illustrates a cross sectional view taken along line 6A—6A of FIG. 6. As presently embodied, a light source 310 projects light in the direction of the arrow A1 onto a character sequence 306 disposed on a surface of the air tube 12. As presently embodied, the character sequence 306 comprises a bar code label or, alternatively, a bar code printed directly onto the air tube 12. The light from the light source 310 reflects from the character sequence 306 in a direction of the arrow A2 and enters a self focusing lens array 313. Light from the self focusing lens array 313 is subsequently focused onto a linear array of photodiodes 315. The linear array of photodiodes generates an electrical output, which is subsequently interpreted by the converter 88 and then by the microprocessor 90 (FIG. 6) to discern calibration information contained within the character sequence 306. According to the presently preferred embodiment, a wedge shaped black plastic holder 318 is disposed between the light source 310, and the self focusing lens array 313, and the linear array of photodiodes 315. The wedge shaped black plastic holder 318 is adapted for securing these three elements 310, 313, and 315 thereto for proper alignment within the housing 14 of the spirometer 10.

Figure 10:
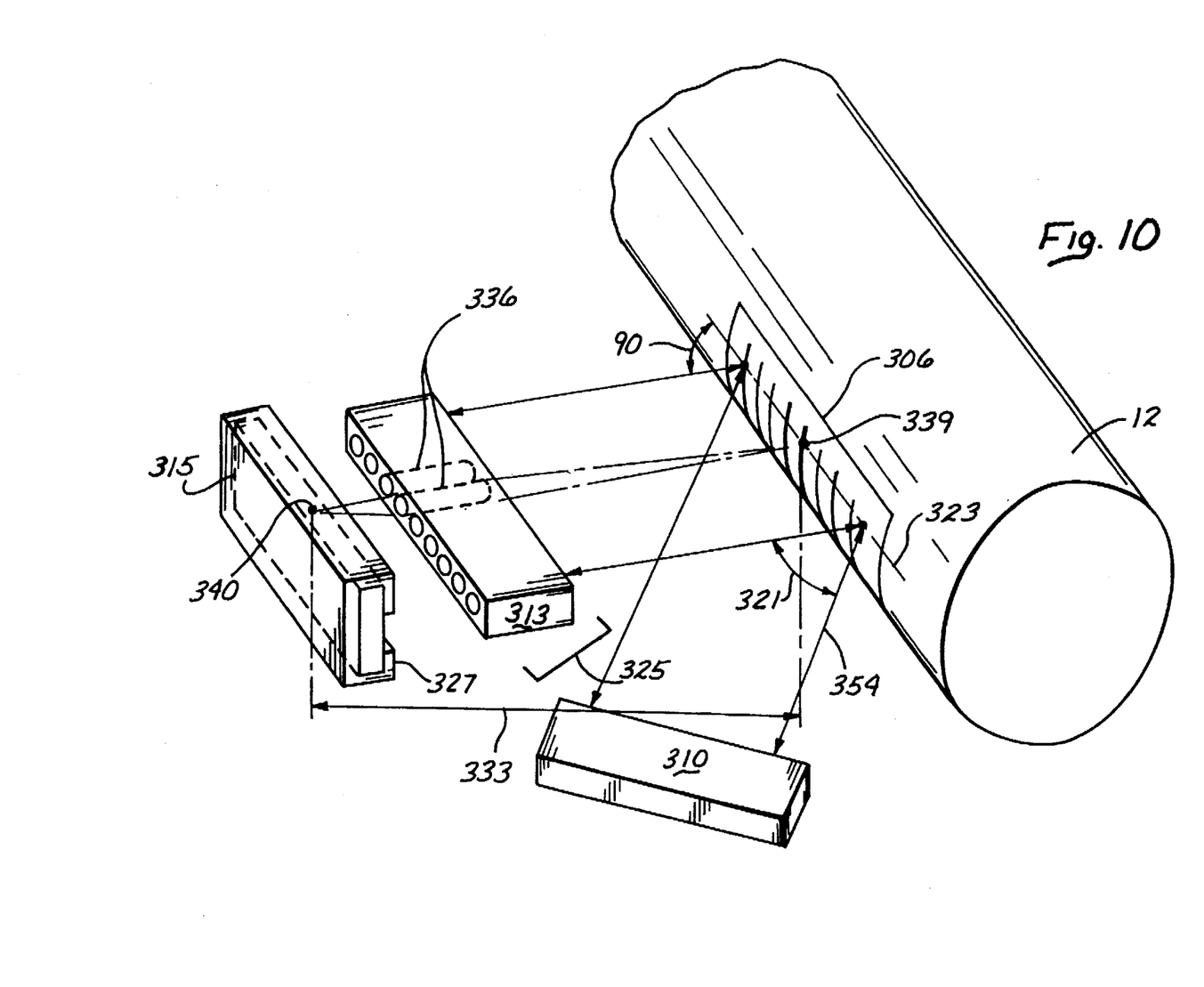
FIG. 10 is a perspective view illustrating the bar code reading assembly of the spirometer of the presently preferred embodiment.

A perspective view of the character recognition unit 304 of the presently preferred embodiment is illustrated in FIG. 10. Light from the light source 310 is focused onto the character sequence 306 disposed on the air tube 12. Reflective light is received by the self focusing lens array 313, which, as presently embodied, is disposed at an angle 321 of approximately 45 degrees from the light source 310. Both the light source 310 and the self focusing lens array 313 have lengths which are substantially parallel to a center line scan 323 passing through the character sequence 306.

The linear array of photodiodes 315 is disposed substantially parallel to the self focusing lens array 313, and is adapted for receiving focused light from the self focusing lens array 313. An extraneous light stop 325 is disposed over a portion of the self focusing lens array 313, and another extraneous light stop 327 is disposed over the linear array of photodiodes 315.

Figure 13:
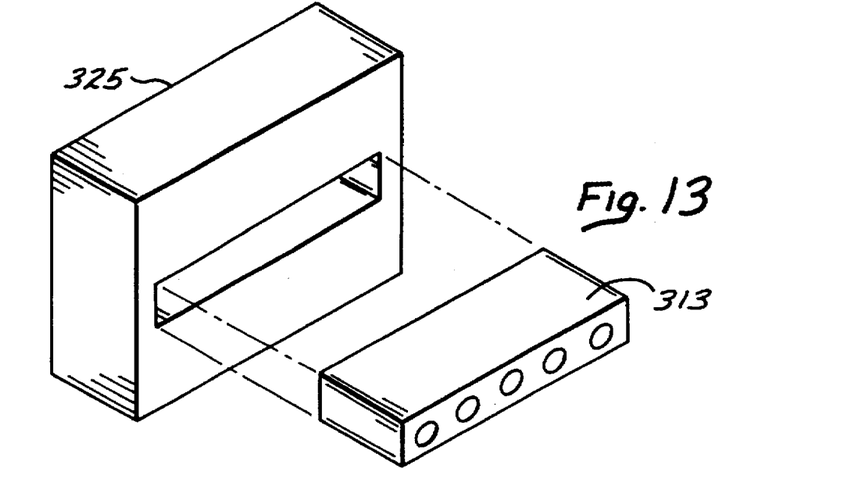
FIG. 13 is a perspective view of a self focusing lens array used for focusing light onto the linear array of photodiodes, according to the presently preferred embodiment.

FIG. 13 illustrates the clip-on light stop 325 adapted for accommodating the self-focusing lens array 313, according to the presently preferred embodiment. The light stop 325 preferably comprises black plastic, and may be frictionally fit around the self-focusing lens array 313 and/or secured thereto using an adhesive. Alternatively, less expensive light stop techniques may be implemented, according to design preference. As mentioned previously with reference to FIG. 6A, both the light source 310 and the self focusing lens array 313 and, more preferably, also the linear array of photodiodes 315, are disposed on a wedge shaped black plastic holder 318. The wedge shaped black plastic holder 318 provides the correct angle between the light source 310, and the self focusing lens array 313 and the linear array of photodiodes 315. The wedge shaped black plastic holder 318 further facilitates proper spacing of the light source 310, the self focusing lens array 313, and the linear array of photodiodes 315 from each other and from the air tube 12. The wedge shaped black plastic holder preferably comprises a black color for suppressing light reflections. The total conjugate focal length 333 of the self focusing lens array 313 is preferably approximately 9.4 millimeters, measured from an internal sensitive surface of the linear array of photodiodes 315 to the target surface of the character sequence 306. As presently embodied, the self focusing lens array 313 comprises a Selfoc® lens array, manufactured by Nippon Sheet Glass Co., Ltd. This self focusing lens array 313 is positioned midway between the linear array of photodiodes 315 and the character sequence 306 so that both the linear array of photodiodes 315 and the character sequence 306 are at focal points of the self focusing lens array 313. As presently embodied, the self focusing lens array 313 is positioned 2.5 millimeters from the character sequence 306 and 2.5 millimeters from the linear array of photodiodes 315.

An approximately 1 millimeter wide portion of the character sequence 306 image along the character sequence center line 323 is transferred by the self focusing lens array 313 to the linear array of photodiodes 315 when the character sequence 306 is illuminated by the light source 310. As presently embodied, the self focusing lens array 313 is approximately 18 to 20 millimeters in length, and comprises a single row of lenses 336. The self focusing lens array 313 is preferably slightly longer than the linear array of photodiodes 315, which is approximately 16 millimeters in length, to insure that the entire linear array of photodiodes 315 receives an image, allowing for a plus or minus 1 millimeter misalignment and/or end lens damage on the self focusing lens array 313. The two focal points of an exemplary individual lens 336 of the self focusing lens array 313, which are not to scale, are shown at 339 and 340.

The linear array of photodiodes 315 preferably comprises an intelligent optical sensor manufactured by Texas Instruments, model number TSL215, and comprising an array of 128 charge-mode pixels in a 128×1 linear array. The linear array of photodiodes 315 is preferred over a charge coupled device (CCD) because of ease of use, among other reasons. The linear array of photodiodes 315 comprises integrated clock generators, analog output buffers, and sample and hold circuitry that would otherwise be required by a CCD circuit. The focal point 340, for example, is focused approximately 1 millimeter beneath the top surface of the linear array of photodiodes 315.

As presently embodied, in addition to the extraneous light stop 327, a clear plastic packaging 344 is disposed over the sensitive surface 346, as illustrated in FIG. 12. The center scan line 323 is projected onto the sensitive surface 346, as shown by the line 348. As presently embodied, the focal point 340 (FIG. 10) is approximately 1 millimeter beneath the top surface of the clear plastic packaging 344, and is projected onto the sensitive surface 346 of the array.

Figure 11:
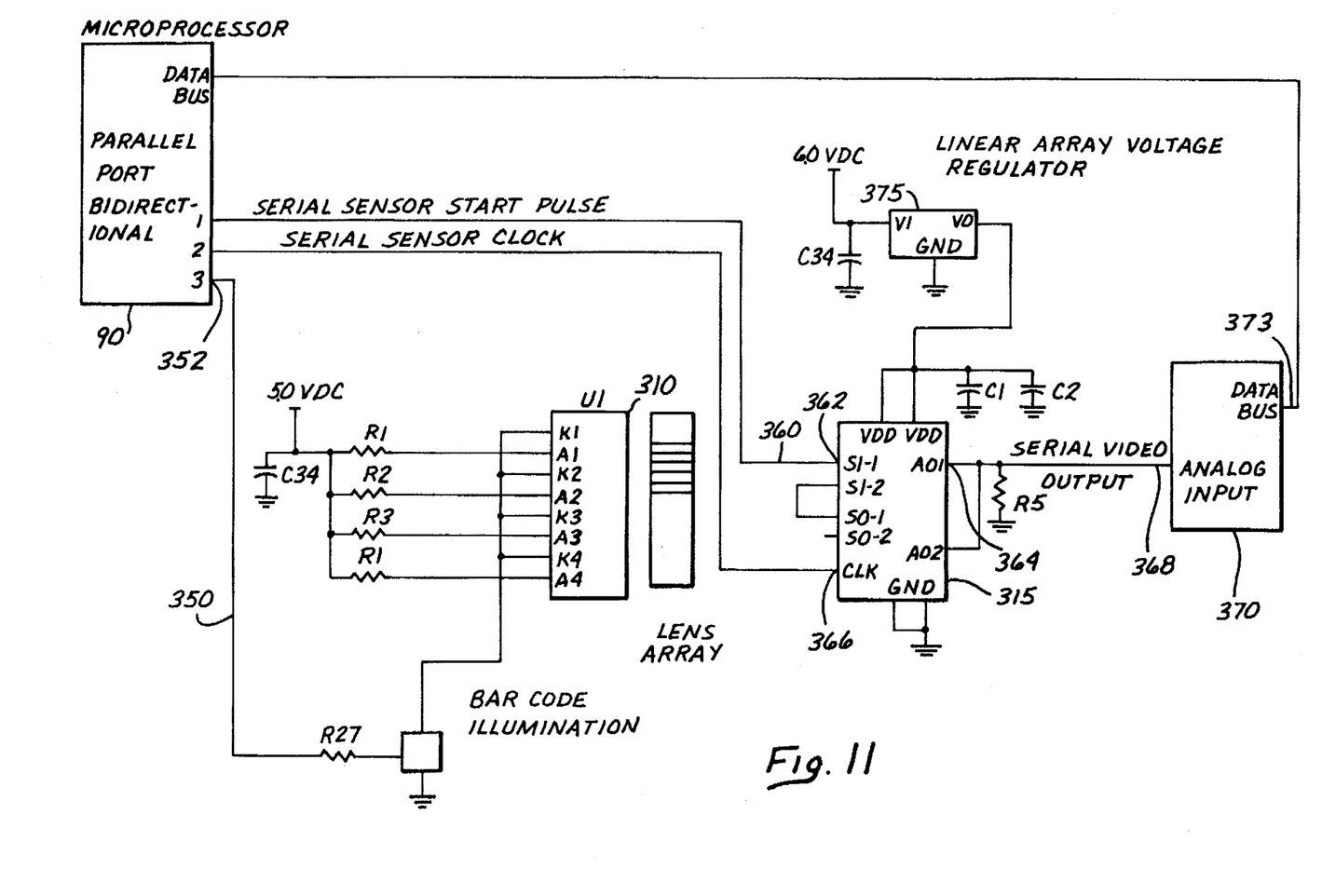
FIG. 11 is a circuit diagram illustrating a specific implementation of the bar code reading assembly of FIG. 10.

Light is projected onto the sensitive surface 346 of the linear array of photodiodes 315 when the light source 310 is activated by the microprocessor 90 (FIG. 6). As illustrated in FIG. 11, the microprocessor 90 activates the light source 310 using the "illumination- on" signal line 350, which is connected to a parallel port pin 352 of the microprocessor 90. As presently embodied, the light source 310 comprises a four element light emitting diode array of approximately 45 millicandelas (lumens/ster), having a wavelength of approximately 635 nanometers and being approximately a lambertian source. The light source 310 is biased with a 20 milliamps of current on the middle two lamps and 25 milliamps of current on the end lamps, to provide an even illumination along the character sequence 306, according to the present invention. The light source 310 provides approximately 23 microwatts per square centimeter of illumination, and is positioned approximately 7 millimeters from the target bar code, as illustrated by reference numeral 354. The light stop 325 between the light source 310 and the self focusing lens array 313 suppresses stray light. The present invention incorporates a 635 nanometer wave length to roughly match the sensor peak responsivity of the linear array of photodiodes 315 which is approximately 750 nanometers. The sensitivity obtained in the linear array of photodiodes 315 is approximately 80% of the 100% maximum linear array sensitivity at 750 nanometers wave length. The light source 310 has a length of approximately 16 millimeters. As presently embodied, the light source 310 is only activated by the microprocessor 90 during bar code reads, since, obviously, activation of the light source 310 dissipates power. Both the light source 310 and the linear array of photodiodes 315 preferably comprise integrated circuits that are mounted on a flexible PC board, and form a dihedral angle 321 with respect to each other of 45%.

Referring to FIG. 11, the image integration time of the linear array of photodiodes 315 begins with a short pulse on line 360 by the microprocessor 90 into the serial input pin 362 of the linear array of photodiodes 315. After approximately 1 to 10 milliseconds, a second serial input pulse is input into the linear array of photodiodes 315 on line 360. After this second serial input pulse, the image is read on the video output pin 364 by clocking the clock pin 366 at between 10 kilohertz and 100 kilohertz, using 129 or more clock pulses. The resulting signal is placed on the serial video output line 368. During the above-mentioned clocking operation, the serial video output, which comprises an analog voltage, is read by the analog to digital (A/D) converter 370, which preferably comprises 12 bit accuracy and a 0 to 5 volt input range. The analog to digital converter 370 outputs digital data on data bus 373, which reflects the amplitude of each video pulse and, consequently, the darkness of each sensor pixel of the linear array of photodiodes 315. This digital data on data bus 373 is subsequently read by the microprocessor 90. The analog to digital converter 370 is controlled by the microprocessor 90, and has a conversion time of approximately 10 microseconds. Accordingly, the linear array of photodiodes 315 can be clocked at up to 10 microseconds (100 kilohertz).

The linear array of photodiodes 315 is powered by a 3 terminal voltage regulator 375 to maintain power supply noise and video array noise at a minimum. Although the Texas Instruments TSL215 is presently preferred, a newer Texas Instruments product, the TSL1402 may be used instead. This later model comprises twice an many pixels in the same length of 16 millimeters. The model has twice the resolution and will allow for more digits and more reliability. This later model is pin compatible, so that the number of clock cycles can simply be changed from 129 to 257, and is less susceptible to optical saturation. The TSL1402 further does not require the 40 millisecond initial pixel charge period, and would provide double the speed and accuracy.

The character sequence 306 preferably comprises a bar code having either an Interleaved 2 of 5 ITF sequence, providing approximately 3 decimal digits of calibration data plus a check sum digit or, alternatively, may comprise a straight binary code. The straight binary bar code is presently preferred, and is configured to provide approximately five and one half digits plus a binary check sum of about six bits. The binary code will be NRZ (non-return-to-zero) with constant width bars and spaces, plus a starting mark. This configuration ensures that the total width of the code is constant and allows 1 millimeter on each side for code positioning error. The minimum white and black bar widths in the bar code are selected to be at least 2 to 3 pixels wide on the linear array of photodiodes 315. Since the linear array of photodiodes has a spacing of 0.125 millimeters between photodiodes, the minimum bar width is approximately twice that width. This configuration ensures that at least one pixel position in the video output 368 of the linear array of photodiodes 315 will go fully low or high, since one pixel in the array 315 is fully black or white, and not positioned half way between a black bar and a white area. The full high or low voltage, in relation to other voltages in the video output 368 of the linear array of photodiodes 315, is decoded by software to positively indicate a bar position.

Since the light source 310 is preferably of constant intensity, variances in light source intensity between units and over time are compensated for by the present invention. For this reason, and to compensate for sensor efficiency, the light integration of the linear array of photodiodes 315 is adjusted. The level of the image video read from the linear array of photodiodes 315 can be increased by increasing the time between the serial input pulses on line 360, i.e., the time of light integration interval. After each bar code read, if the bar code amplitude data is too low, the integration time is adjusted up until the amplitude is sufficient to detect white to black differences. The overall amplitude of the whole serial video data stream from each read operation forms a nonlinear curve, due to changes in light intensity along the light source. In software, according to the present invention, a running differential average or other indicator indicates the approximate white to black threshold along the entire video data length. This average will be used to detect white from black data by software comparison. High frequency noise is filtered out by software, and the resulting data stream comprises an image of the bar code. As presently embodied, this resulting data stream is decoded by the NRZ binary method or the interleaved 2 of 5 method, depending on the code used. This NRZ format changes the bar code color if the data bits do not change and does not change the bar code color when the bits do change. The resulting steam, after being decoded by either the NRZ binary method or the integrated 2 of 5 method, comprises the original binary or decimal number that was originally encoded onto the air tube 12. This number is then used to calibrate this spirometric flow sensor.

The linear array of photodiodes 315 must initially be preconditioned by a 40 millisecond operation period, before each bar code read, to thereby allow for each of the 128 pixels to change from white to black or vice versa, correctly. During this preconditioning period, the light source remains on, and the data from the bar code is ignored. Subsequently, several bar code scans are performed until the correct data is obtained, judging by the check sum embedded in the bar code. According, the total read operation is approximately 40 milliseconds plus 5 milliseconds per bar code scan, or about milliseconds. Each bar scan requires 128 times 10 microseconds minimum time, or 128 times 100 microseconds maximum time. The time is determined by the required integration time, as mentioned above.

The light source 310 is turned on continually during all bar code scans, up to 100 milliseconds, and is not turned off between individual 5 millisecond scans, since the pixels have to be illuminated throughout the integration time. An embedded microprocessor 16 bit timer is programmed to develop 10 to 100 milliseconds repeated time periods, with each period generating an interrupt. A timer interrupt starts a routine that outputs the integration start pulse if needed, and then outputs 129 clock pulses, timed by the timer. At each clock pulse, the analog to digital converter 370 is read by the microprocessor 90 via data bus 373 and stored for later analysis. After completion of the 129 clock pulses, the timer is stopped and the data is analyzed by the microprocessor 90 to find the moving white-black threshold level, for each pixel, using continuous filtering and averaging. The data is then filtered in software and compared to the moving threshold level, before being converted into bar codes. In the presently preferred embodiment, approximately 8 bar code scans are taken and stored at a time, requiring 8 times 12.5 milliseconds, or 100 milliseconds maximum time, so that the 40 milliseconds initial pixel charge time does not have to be repeated.

Regarding the self-focusing lens array 313, this assembly may have to be adjusted to focus exactly on the character sequence 306 within plus or minus 0.3 millimeters, unless this is guaranteed by the manufacturing process. The focal distance may have to be adjusted in a low light environment, while a diagnostic program runs on the microprocessor 90 and continually scans the character sequence 306, outputing the percentage of read errors from reading the character sequence 306. This focal distance is preferably adjusted until the errors are minimized. Worst case or random bar code examples would preferably be used for this procedure.

According to the method of calibrating a subject air tube 12 and placing the calibration information onto the air tube 12 in the form of a character sequence 306, a large initial sample lot of air tubes 12 from a manufacturing line are tested. As presently embodied, the testing procedure comprises subjecting each flow tube 12 to an air stream of 7.5 liters per second in the expiratory direction. A sensor leg, similar to that shown in FIG. 6 at 76, is placed over the through port 24 (FIG. 2) of the air tube 12, and this sensing leg is connected to a high-accuracy pressure sensor. A mechanical resonance filter may be required in the tube. The measured pressure, in response to the air stream of 7.5 liters per second in the expiratory direction, is noted for each tube and, subsequently, a similar measured pressure for the same air flow rate in the inspiratory direction is obtained for each air tube 12.

The present invention recognizes that, although manufacturing differences exist between each air tube 12, the pressure output versus airflow input curve for each air tube 12 is remarkably similar. More particularly, this pressure output versus air flow input curve for each flow tube 12 can be mathematically modeled by a third order polynomial with fixed coefficients. The polynomial for each air tube 12 varies by only a single gain factor. Thus, according to the presently preferred embodiment, the response of any subject air tube may be calibrated to replicate an ideal or model response by merely multiplying the response of the subject air tube by a constant.

Since the pressure output versus air flow input curve for each air tube 12 varies only by a constant, the measured pressure of a subject air tube 12 can be compensated to achieve an ideal pressure output, for any given air flow rate between 0 and 16 liters per second. Although the present invention is described in a particular embodiment where calibration of each subject air tube can be performed by merely generating a single calibration constant for each air flow direction (inspiratory and expiratory), the present invention is not limited to this exemplary embodiment.

According to the presently preferred embodiment, after pressure measurements for air flow rates in the inspiratory direction and the expiratory direction are obtained for a subject air tube 12, these two pressure measurements are compared with two corresponding model pressure measurements. The model pressure measurements are obtained by averaging pressure measurements of a large initial sample lot of flow tubes 12 from the manufacturing line, as presently preferred. A gain factor is determined, based upon the tube pressure measurement of the subject air tube 12 and the tube model pressure measurements. For example, if the model pressure measurement for the inspiratory direction is slightly higher than the subject tube pressure measurement for the inspiratory direction, a correction factor is generated to increase the pressure measurement of the subject tube 12 to the model pressure measurement. This correction factor comprises a constant in the presently preferred embodiment. A look-up table having a number of subject-air-tube 12 measurements and corresponding correction factors may be used, as Just one example. As presently embodied, such a look-up table may comprise a large number of subject tube pressure measurements according to desired accuracy, and corresponding correction factors. The correction factors, as presently embodied, calibrate each subject tube to a desired accuracy level. Still further, according to the presently preferred embodiment, a single binary number is used to represent both correction factors for any subject air tube 12. Since the subject air tube 12 is tested for a measured pressure in both the inspiratory direction and the exptratory direction, two different correction factors will be generated, corresponding to the two measured pressure rates of the subject air tube 12. The single binary number is presently preferred to represent these two correction factors in a compressed form, and may also be obtained from a look-up table.

Figure 14:
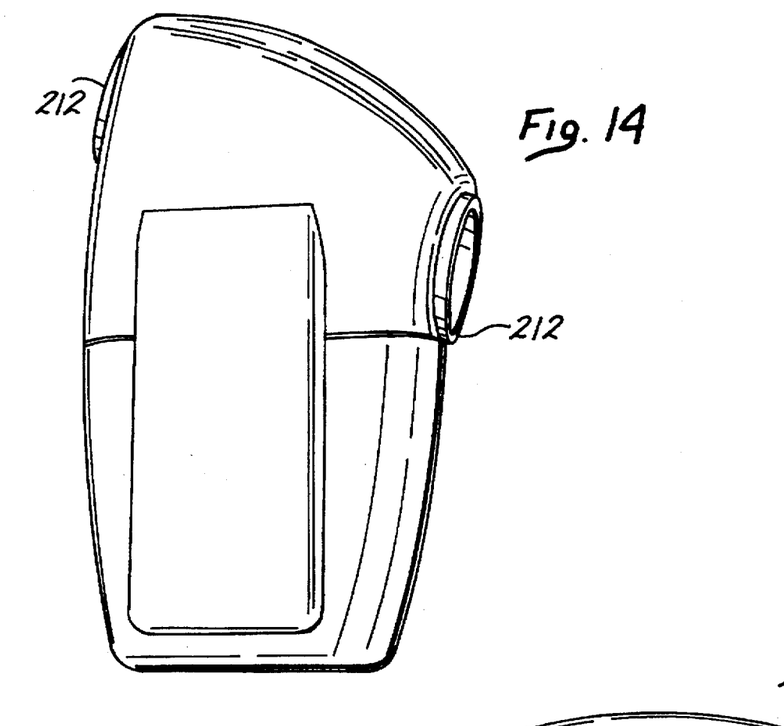
FIGS. 14 and 15 illustrate perspective views of a spirometer design according to the presently preferred embodiment.
Figure 15:
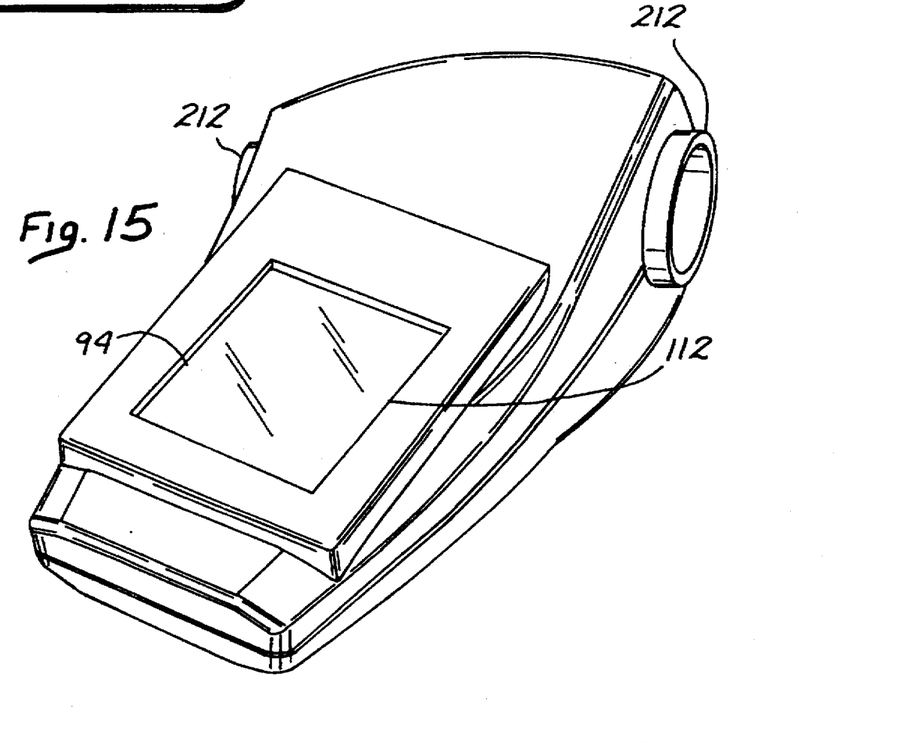

FIGS. 14 and 15 illustrate perspective views of a spirometer design according to the presently preferred embodiment. The air tube 212 is substantially covered by the housing, and the display 94 and transparent-overlay keypad 112 are larger than in previously described embodiments.

While this invention has been described with respect to various specific examples and embodiments, it is to be understood that the invention is not limited thereto and that it can be variously practiced with the scope of the following claims.

What is claimed is:

1. A spirometer adapted for holding an air tube, the spirometer comprising:
    a frame adapted for removably holding an air tube having a pressure response and machine-readable calibration information relating to the pressure response of the air tube;

a pressure sensing assembly adapted to sense a pressure in the air tube held by the frame and to provide pressure data based at least in part on the pressure in the air tube;

a character recognition unit adapted for automatically reading the calibration information; and circuitry adapted to automatically process the calibration information read by the character recognition unit, the circuitry being adapted to use the read calibration information to automatically correct the pressure response of the air tube held by the frame to a pressure response of a model air tube having a configuration and dimensions which are substantially similar to the air tube held by the frame.

2. The spirometer as recited in claim 1, the character recognition unit comprising a bar code reader.

3. An air tube having a pressure response and being adapted for use in a spirometer, the air tube comprising:

a tubular member; and machine-readable calibration information adapted to automatically relate the pressure response of the air tube to a model pressure response of a model air tube having dimensions which are substantially similar to the air tube, the machine-readable calibration in information excluding alpha-numeric text.

4. The air tube as recited in claim 3, the calibration information comprising a bar code format.

5. The air tube as recited in claim 3, the air tube being disposable and the calibration information being disposed on the tubular member.

6. The air tube as recited in claim 3, the calibration information being adapted to facilitate generation of a corrected pressure response of the air tube, the corrected pressure response taking into account the model pressure response of the model air tube.

7. The air tube as recited in claim 3, the tubular member having an outer surface and including at least one pressure port.

8. A spirometer comprising:

a frame adapted for removably holding an air tube having both a pressure port and machine-readable calibration information;

a pressure sensing assembly adapted to sense the pressure in the pressure port of the air tube held by the frame and to provide pressure data based at least in part on the pressure in the pressure port; and circuitry adapted to automatically read the calibration information of the air tube and to automatically adjust the pressure data to that which would have been generated by the pressure sensing assembly sensing a pressure of a model air tube having dimensions and a configuration which are substantially similar to the air robe held by the frame.

9. An air tube having a pressure response for use in a spirometer, the air tube comprising:

a tubular member defining a hollow space; and machine-readable adjustment information adapted to facilitate an automatic adjustment of the pressure response of the air tube based at least in part upon a model pressure response of a model air tube having dimensions which are substantially similar to the air tube, the machine-readable adjustment information excluding alpha-numeric text.

10. The air tube as recited in claim 9, the adjustment information comprising a bar code format.

11. The air tube as recited in claim 9, the air tube being disposable and the adjustment information being disposed on the tubular member.

12. The air tube as recited in claim 9, the adjustment information being effective in providing a corrected pressure response of the air tube, the corrected pressure response taking into account the model pressure response of the model air tube.

13. The air tube as recited in claim 9, wherein the tubular member has an outer surface and includes at least one pressure port.

* * * * *